(12) United States Patent
Fly et al.

(10) Patent No.: US 6,828,053 B2
(45) Date of Patent: Dec. 7, 2004

(54) IN-SITU RESISTIVE CURRENT AND TEMPERATURE DISTRIBUTION CIRCUIT FOR A FUEL CELL

(75) Inventors: Gerald W. Fly, Geneseo, NY (US); Michael W. Murphy, Manchester, NY (US); Robert L. Fuss, Spencerport, NY (US); Lewis J. DiPietro, Rochester, NY (US)

(73) Assignee: General Motors Corporation, Detroit, MI (US)

( * ) Notice: Subject to any disclaimer, the term of this patent is extended or adjusted under 35 U.S.C. 154(b) by 196 days.

(21) Appl. No.: 10/206,140

(22) Filed: Jul. 26, 2002

(65) Prior Publication Data

US 2004/0018401 A1 Jan. 29, 2004

(51) Int. Cl.[7] .................................................. H01M 8/04
(52) U.S. Cl. ............................. 429/32; 429/12; 429/18; 204/401
(58) Field of Search .............................. 429/18, 12, 32; 204/401

(56) References Cited

U.S. PATENT DOCUMENTS 6,541,147 B1    4/2003  McLean et al.

2002/0090540 A1 *  7/2002  Einhart et al. ................ 429/32
2002/0094460 A1 *  7/2002  Horlop ......................... 429/13
2004/0048113 A1 *  3/2004  Murphy et al. .............. 429/13

OTHER PUBLICATIONS

S.J.C. Cleghorn, C.R. Derouin, M.S. Wilson, S. Gottesfeld; A Printed Circuit Board Approach To Measuring Current Distribution In A Fuel Cell; Journal of Applied Electrochemistry 28 (1998) 663–672, no month.

* cited by examiner

Primary Examiner—John S. Maples
(74) Attorney, Agent, or Firm—Cary W. Brooks, Esq; Linda M. Deschere, Esq.

(57) ABSTRACT

A sensor plate for measuring current and/or temperature distribution of an operating fuel cell. The sensor plate has a circuit board interposed between an anode flow field plate and a cathode flow field plate of the fuel cell. A flow field plate is segmented into a plurality of electrically isolated regions without disrupting the flow field of the plate. The circuit board has an array of resistors and/or thermistors mounted to it wherein each resistor and/or thermistor is associated with one of the electrically isolated regions of the segmented plate. The current distribution of the electrically isolated regions of the fuel cell is calculated by using the voltage drop across the resistors and the known resistance values of the resistors mounted to the circuit board.

24 Claims, 9 Drawing Sheets

US 6,828,053 B2

IN-SITU RESISTIVE CURRENT AND TEMPERATURE DISTRIBUTION CIRCUIT FOR A FUEL CELL

FIELD OF THE INVENTION

The present invention relates to fuel cells and, more particularly, to a sensor plate for measuring an operating parameter such as current or temperature of a cell in a fuel cell stack.

BACKGROUND OF THE INVENTION

Fuel cell stacks are electro-chemical energy conversion devices that use a hydrogen fuel and oxygen to produce electricity with water and heat as by-products. A fuel cell stack typically includes a plurality of individual fuel cells arranged in a stacked relation. Each fuel cell includes an anode flow field plate, a membrane electrode assembly (MEA) and a cathode flow field plate. A coolant layer may optionally be included.

An oxidant gas, such as oxygen or air, is supplied to the cathode flow field plate. A fuel, such as hydrogen, is supplied to the anode flow field plate of the fuel cell. As the hydrogen gas flows through the anode flow field plate, the hydrogen gas is separated on an anode catalyst on the MEA into positively charged hydrogen ions and negatively charged free electrons. The hydrogen ions pass through a proton exchange member (PEM) of the MEA where the ions combine with oxygen on a cathode catalyst to produce water. When multiple fuel cells are used to form a stack, the electricity produced by each cell is transmitted through the fuel cell stack and collected by external circuitry. Since the reaction which takes place in the fuel cell stack is exothermic, a coolant layer may be used to remove heat from the fuel cell by supplying and exhausting a coolant fluid.

Various flow field plate designs have been used to form fuel cells with the design being dictated by the particular application. To determine the efficiency of each flow field, the design is incorporated into the anode and cathode flow field plates to form a fuel cell which is then used in a fuel cell stack. Determining the current distribution and temperature distribution at various locations within the flow field can provide insight into the effectiveness of that flow field plate design. Also, certain operating conditions cause variations in the distribution of the current and temperature of a fuel cell. Knowing the current and temperature distributions during various operating conditions allow for testing of fuel cells to evaluate the efficiency of the design. Accordingly, there is a need in the art to provide an in-situ sensor plate for measuring the current and temperature distribution of an operating fuel cell.

SUMMARY OF THE INVENTION

The present invention is directed to an apparatus for measuring current and temperature distribution of an operating fuel cell within a fuel cell stack.

The present invention includes a sensor assembly having a sensor plate. The sensor plate comprises a first flow field plate segmented into an array of electrically isolated regions, a second flow field plate, and a circuit board interposed between the first and second flow field plates. The circuit board has a resistor array with a resistor associated with each of the electrically isolated regions for measuring the current and/or temperature associated with each individual segment, thereby providing a current and/or temperature distribution across the major face of the fuel cell.

Further areas of applicability of the present invention will become apparent from the detailed description provided hereinafter. It should be understood that the detailed description and specific examples provided therein, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment is merely exemplary in nature and is in no way intended to limit the invention, its application, or uses.

The present invention provides a means to monitor the current distribution of an operating fuel cell using a sensor plate. In an assembly according to the invention, the anode and cathode flow field plates of a fuel cell bipolar plate are electrically separated from one another with an array of resistors between such anode and cathode flow field plates. The method of the invention relies upon the relationship between the current traveling through any resistor of the array and the current leaving a region of the membrane electrode assembly (MEA) directly adjacent to that resistor. Then, the distribution of the current leaving an entire fuel cell is determinable by the array of resistors across the entire cross-sectional area of the cell. Given the resistance of each resistor being a known value, the current passing through a particular resistor is determined by measuring the voltage drop across such resistor. In this manner, the current produced by an MEA is determined as a function of position, by measuring the voltage drops across each resistor in the array. In other words, current as a function of position across the MEA, is monitored.

An equivalent approach is used to monitor the temperature distribution of a fuel cell. In one alternative, the array comprises temperature-sensing resistors, that is, thermistors, with each thermistor associated with a different region of the MEA. In another alternative, the assembly comprises respective arrays of thermistors and current-sensing resistors. The method of the invention relies upon the relationship between the temperature sensed by a thermistor being representative of the temperature of a region of the MEA directly adjacent to that thermistor. Then, the distribution of the temperature across an entire fuel cell is determinable by the array of thermistors across the entire cross-sectional area of the cell. Given the temperature coefficient of each thermistor being a known value, the temperature of each thermistor is determined by measuring the voltage drop across each thermistor. In this manner, the temperature of an MEA is determined as a function of position by measuring the voltage drops across each thermistor in the array. In other words, temperature as a function of position across the MEA, is monitored.

Figure 1:
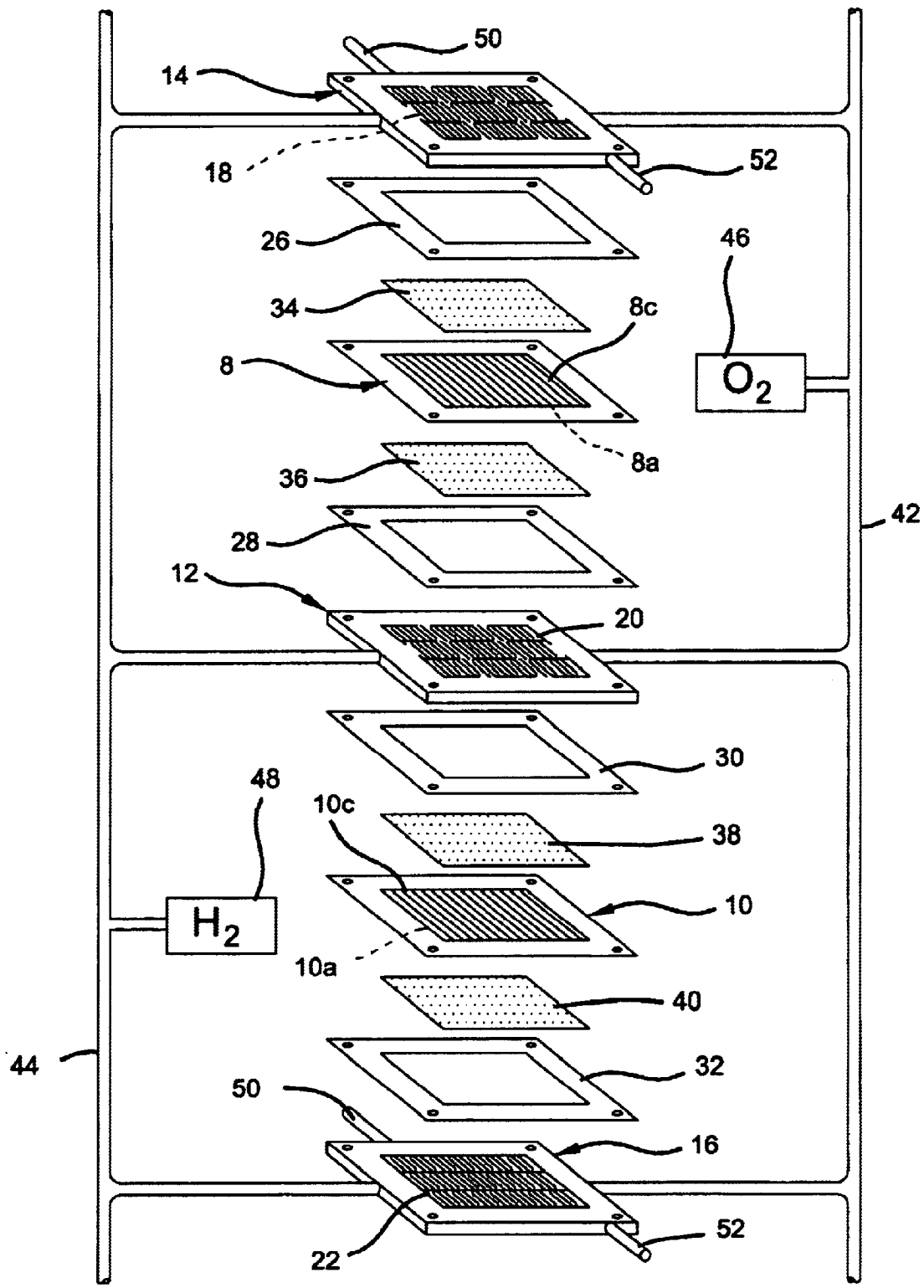
FIG. 1 is an exploded illustration of a fuel cell incorporating the sensor plate of the present invention.

By way of background, FIG. 1 schematically depicts a partial fuel cell stack 6 having a pair of MEAs 8 and 10 separated from each other by a non-porous, electrically-conductive bipolar plate 12 which includes the sensor plate of the present invention. Each of the MEAs 8, 10 have a cathode face 8c, 10c and an anode face 8a, 10a. The MEAs 8, 10, and bipolar plate 12, are stacked together between non-porous, electrically-conductive bipolar plates 14, 16. The plates 12, 14, 16 each include flow fields 18, 20 and 22 having a plurality of flow channels formed in a face of the plates for distributing fuel and oxidant gases (i.e., $H_2$ & $O_2$) to the reactive faces of the MEAs 8, 10.

Porous, gas permeable, electrically-conductive sheets 34, 36, 38, 40 press up against the electrode faces of the MEAs 8, 10 and serve as primary current collectors for the electrodes. Primary current collectors 34–40 also provide mechanical support for the MEAs 8, 10, especially at locations where the MEAs are otherwise unsupported in the flow field. Bipolar plates 14, 16 press up against the primary current collector 34 on the cathode face 8c of MEA 8 and the primary current collector 40 on the anode face 10a of MEA 10, respectively. Bipolar plate 12 presses up against the primary current collector 36 on the anode face 8a of MEA 8 and against the primary current collector 38 on the cathode face 10c of MEA 10.

An oxidant gas, such as oxygen or air, is supplied to the cathode side of the fuel cell stack 6 from a storage tank 46 via appropriate supply plumbing 42. In a preferred embodiment, the oxygen tank 46 may be eliminated and air supplied to the cathode side from the ambient environment. A fuel, such as hydrogen, is supplied to the anode side of the fuel cell stack 6 from a storage tank 48 via appropriate supply plumbing 44. In a preferred embodiment, the hydrogen tank 48 may be eliminated and the anode feed stream may be supplied from a reformer which catalytically dissociates hydrogen from a hydrocarbon fuel. Exhaust plumbing (not shown) for the reactant gases exhausted from the fuel cell stack 6 is also provided for removing anode effluent from the anode flow field and cathode effluent from the cathode flow field. Coolant plumbing 50, 52 is provided for supplying and exhausting a coolant fluid to the bipolar plates 12, 14, 16, as needed.

Figure 2A:
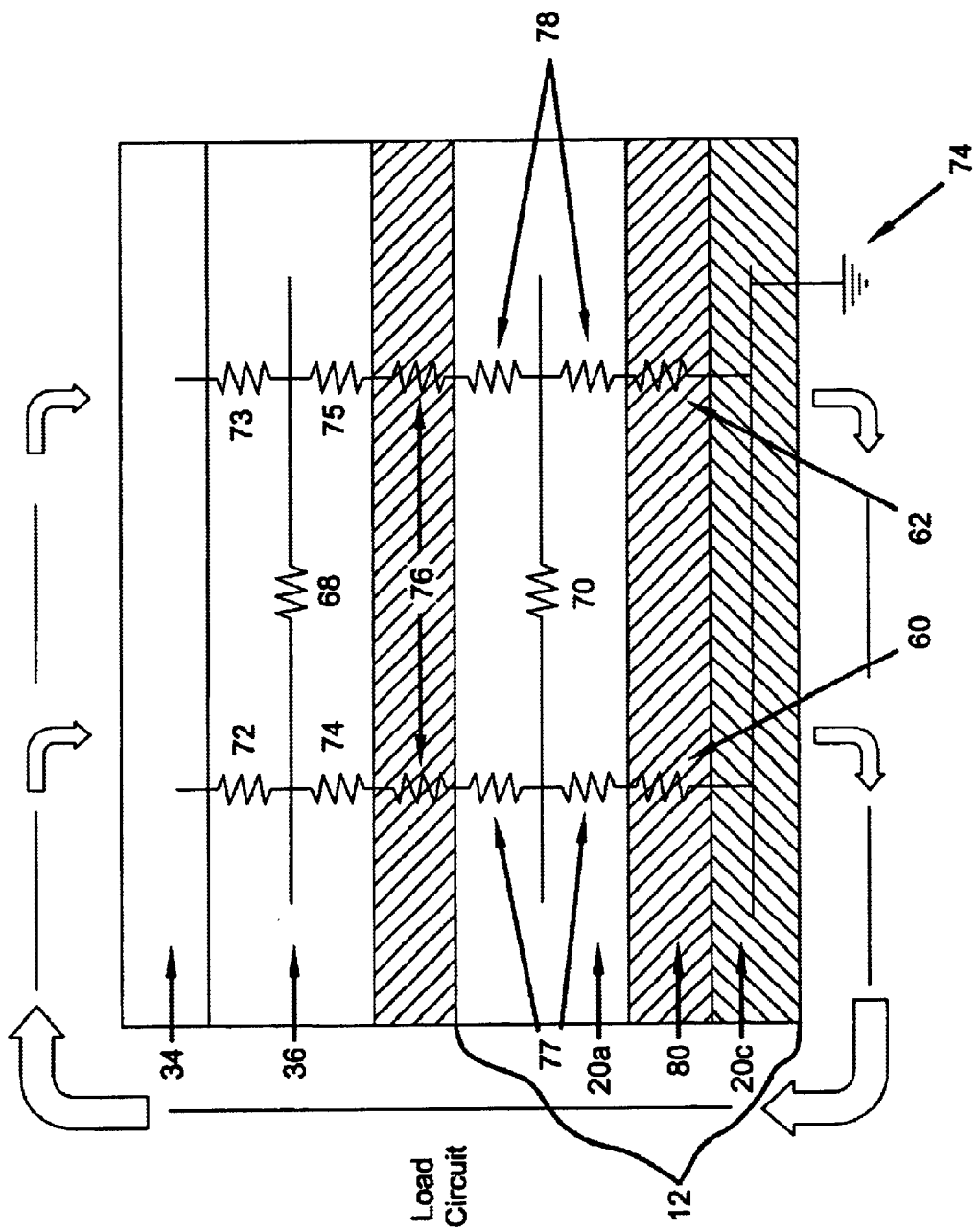
FIG. 2A is a schematic representation of the current flow path through a fuel cell having the sensor plate of the present invention.

FIG. 2A is a schematic illustration of the current flow path through a fuel cell assembly that includes the current distribution sensor plate 12. The load circuit of the invention is the current produced by the operation of the fuel cell. Sensor plate 12 comprises a cathode flow field plate 20c, an anode flow field plate 20a, and a circuit board 80. Circuit board 80 comprises an array of current-sensing resistors 60, 62 that connect the anode and cathode flow field plates 20a, 20c. Above the anode flow field plate 20a is a diffusion media sheet 36. In FIG. 2A, reference number 76 represents the electrical contact resistance between anode flow field plate 20a and diffusion media sheet 36. Above the diffusion media sheet 36 sits MEA 34, which is the element for which the current distribution is being measured.

Each of the physical elements of the assembly shown in FIG. 2A have a nominal electrical resistance associated with them. The resistance value of a particular element of the assembly can also be anisotropic, meaning that an element's resistance in the through-plane direction may be different from its resistance in the in-plane direction. Because of this, each physical element has separate reference numbers representing the respective electrical resistance in the in-plane and through-plane directions. The areas of resistance in the in-plane and through-plane directions function as resistive elements. These terms are used interchangeably herein.

As described earlier, the method of the invention relies upon the relationship that the current traveling through a particular current-sensing resistor 60, 62 is representative of the same value of current that is leaving the region of the MEA 34 directly above that current-sensing resistor 60, 62. This relationship is a function of the contact resistance or inherent resistive values in each of the assembled elements. Accordingly, it is assumed that most of the current entering diffusion media 36 at the area associated with reference number 72 leaves circuit board 80 through the current-sensing resistor 60. Similarly, most of the current entering diffusion media 36 at the area represented by reference number 73 leaves circuit board 80 through current-sensing resistor 62. Thus, only a small portion of the current travels laterally through areas represented by reference numbers 68 and 70. In order for the method of the invention to operate in this manner, the values of current sense resistors 60 and 62 must be selected to have relatively low resistance values with respect to the values of the through-plane bulk and contact resistances 74, 75, 76, 77, and 78, and the in-plane resistance values of the areas represented by reference numbers 68 and 70.

Figure 4:
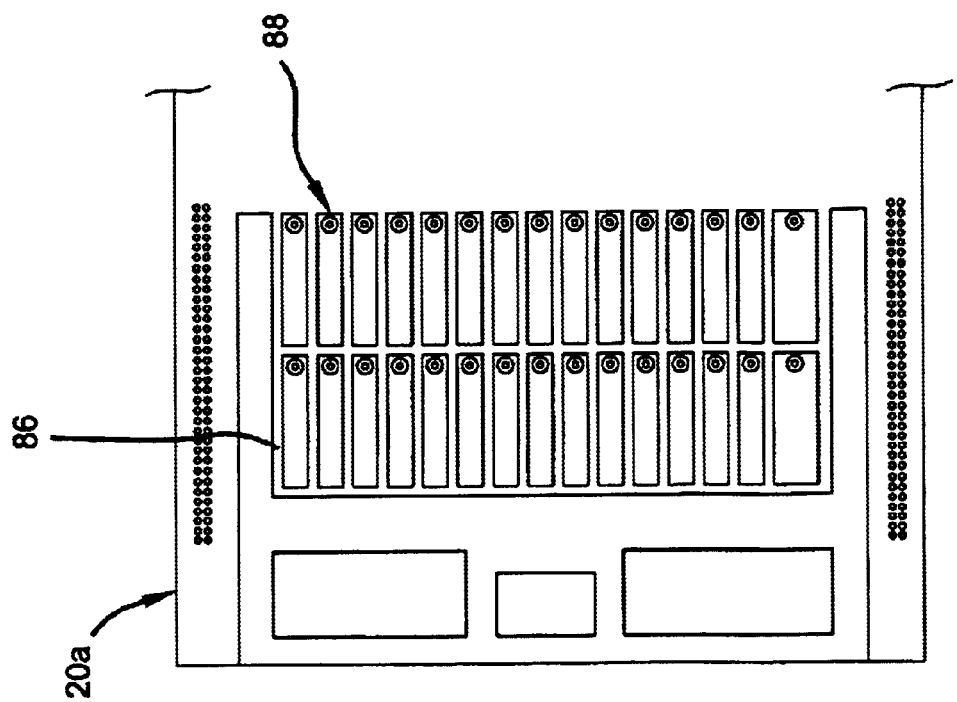
FIG. 4 is a top view of a portion of the first flow field plate segmented into a plurality of electrically isolated regions and having connection points for the first connection lead of a resistor.

Accordingly, the relative resistance values of each bulk region associated with reference numbers 70, 77, and 78 of the anode flow field plate 20a are much lower than any other resistors in the network. The anode flow field plate 20a has a relatively low in-plane resistance value represented by reference number 70 (typically on the order of 100 $\mu\Omega$) which readily allows current to travel in the through-plane direction of the anode flow field plate 20a instead of being transmitted in the in-plane direction. For this reason, the area represented by reference number 70 must be segmented or electrically isolated to eliminate the in-plane current flow. FIG. 4 illustrates the segmentation of a portion of the anode flow field plate 20a that takes place in order to electrically isolate this current path. Segmenting the anode flow field plate 20a effectively removes the low resistance area represented by reference number 70 from the circuit, creating electrically isolated regions for the current paths.

The present invention describes using the anode flow field plate 20a as the segmented plate. Segmenting the field associated with the fuel (i.e., the anode flow field plate)

minimizes the disturbance of the reactant gases flowing through the fuel cell. However, a skilled practitioner will recognize that the present invention could utilize a segmented cathode flow field plate 20c in place of or in addition to the segmented anode flow field plate 20a.

Figure 2B:
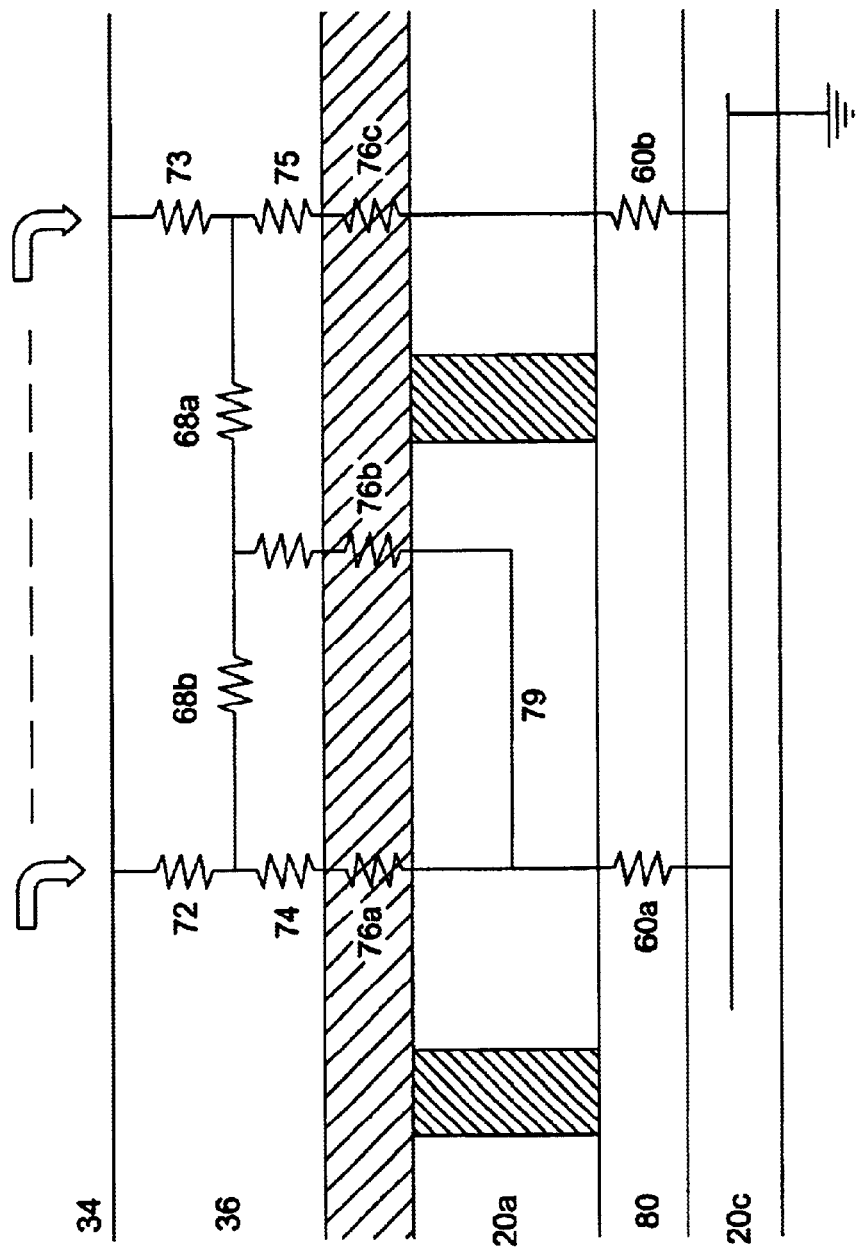
FIG. 2B is a schematic representation of alternative current flow paths through a fuel cell having a sensor plate.

Referring back to FIG. 2A, the resistance to current travel through the diffusion media 36, represented by reference number 68, is, on the other hand, large enough (typically in the range of 80–100 mΩ) so that the electrical leakage path can remain connected without substantially reducing measurement accuracy. The leakage path represented by reference number 68 is, in fact, two parallel pathways. Both are schematically illustrated in FIG. 2B.

Both pathways cross from one segmented region of the anode flow field plate 20a to the next through the region of the diffusion media 36 that sits over the gap where the anode flow field plate 20a was segmented. This electrical pathway is represented by reference number 68a. However, current may be delivered to the area represented by reference number 68a through two different paths: one path allows current to travel through the diffusion media 36 to the next through-plane path of the fuel cell, and the other path allows current to jump from the diffusion media 36 down into the anode flow field plate 20a, across the anode flow field plate 20a to the edge of the segmented region, then back up into the diffusion media 36.

After current has passed through the areas represented by reference number 72 it is desired that that same current travel through the bulk regions represented by reference numbers 74 and 76a in order to become measured by the current-sensing or shunt resistor 60a. However, leakage to current-sensing or shunt resistor 60b is still possible through the diffusion media 36, as shown by the area represented by reference number 68b and 68a. Current will attempt to travel to another through-plane path of the fuel cell represented by reference numbers 75, 76c, and 60b via a pathway in the diffusion media 36 represented by reference numbers 68b and 68a. However, this path does not diminish measurement accuracy. Current does not travel through this path because the in-plane resistance represented by reference numbers 68b and 68a of the diffusion media 36 is higher than that of the through-plane resistance represented by reference number 74, 76a, and 60a. This higher resistance is due to the distance that current must travel to reach the next through-plane path and the thinness of the diffusion media layer 36.

Reference numbers 74, 76a, 76b, and 79 represent the second pathway in which current can travel through the anode flow field plate 20a. This path does not diminish measurement accuracy because the contact resistance represented by reference numbers 76a, 76b, and 76c between the diffusion media 36 and the anode flow field plate 20a raises the resistance of this path. For the above two reasons, the electrical path represented by reference numbers 68a and 68b need not be cut, thus avoiding the need to segment the diffusion media layer 36.

Referring back to FIG. 2A, the circuit board 80 is constructed of a non-conductive material, thereby causing no current leakage across the circuit board 80. Each current-sensing resistor 60, 62 on the circuit board 80 has a first connection lead coupling the current-sensing resistor 60, 62 to the anode flow field plate 20a. The current-sensing resistor 60, 62 will also have a second connection lead coupling the current-sensing resistor 60, 62 to a common or ground 74. In another embodiment of the invention, a second connection lead couples the current-sensing resistor 60, 62 to the cathode flow field plate 20c.

As previously discussed, the resistor values used in the sensor plate 12 should be low relative to the in-plane resistance represented by reference number 68 of the diffusion media 36. As presently preferred, resistor 60, 62 should be an order of magnitude less than the diffusion media 36 (typically in the range of less than 10 mΩ). Thus, the area of the diffusion media 36 represented by reference number 68 will determine the resistor value of the sensor plate 12. As the resistance of the current-sensing resistor 60, 62 approaches the bulk resistance of the diffusion media 36, current is re-distributed through the diffusion media 36 instead of through current-sensing resistor 60, 62 of the sensor plate 12. If such distribution occurs, the sensor plate 12 becomes ineffective for measuring current within the segmented regions and instead provides an overall average current distribution across the face of the cell instead of the desired current measurement of each segmented region.

Figure 3:
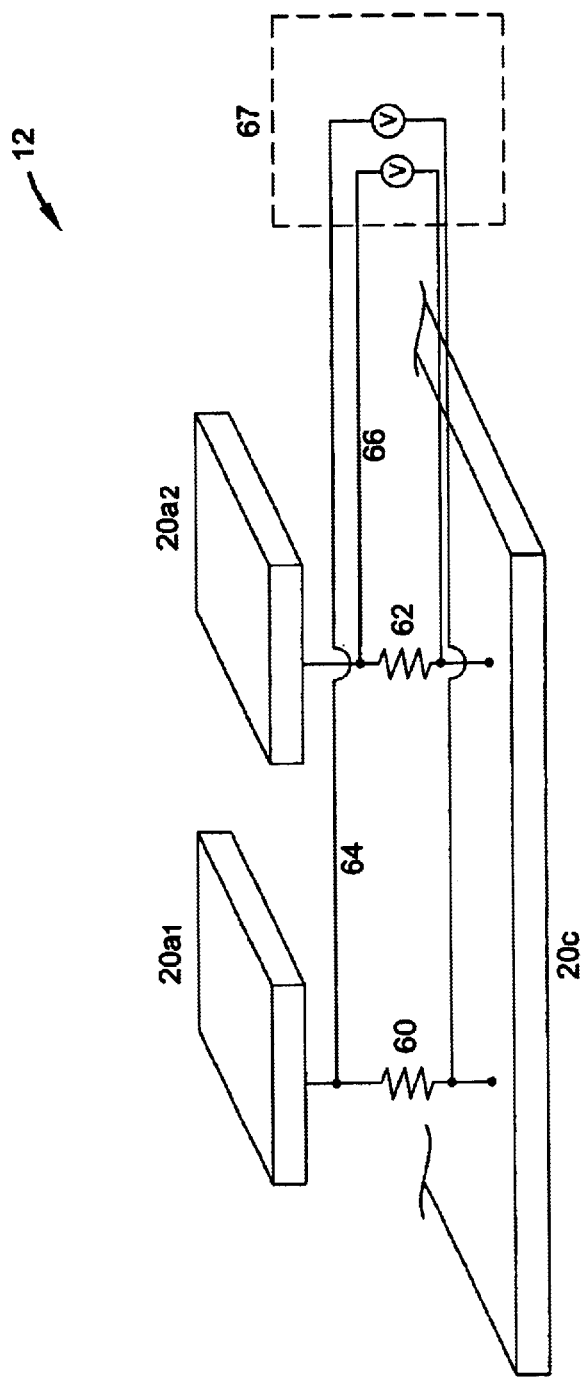
FIG. 3 is a schematic of the instrumentation for monitoring the voltage drop across each current sense resistor.

FIG. 3 is an electrical schematic of the current distribution sensor plate 12 that includes an illustration of the monitoring instrumentation used to measure the voltage drop across each current-sense resistor 60, 62. As described earlier, electrically isolated regions of the anode flow field plate, $20a_1$ and $20a_2$, are electrically connected to cathode flow field plate 20c through known value current-sensing resistors 60 and 62. Each resistor 60, 62 is connected to a pair of voltage sense leads, 64 and 66, via contact pads (not shown), and extend out of the sensor plate 12 to a high-channel count DC voltmeter 67. A DC voltmeter 67 is used to convert analog measurements of the voltage drop across each current-sense resistor 60, 62 into digital values that indicate the amount of current leaving the region of the MEA 34 directly adjacent to each particular resistor 60, 62. By displaying these values in the form of an intensity plot, the current distribution of a fuel cell is revealed.

Figure 5:
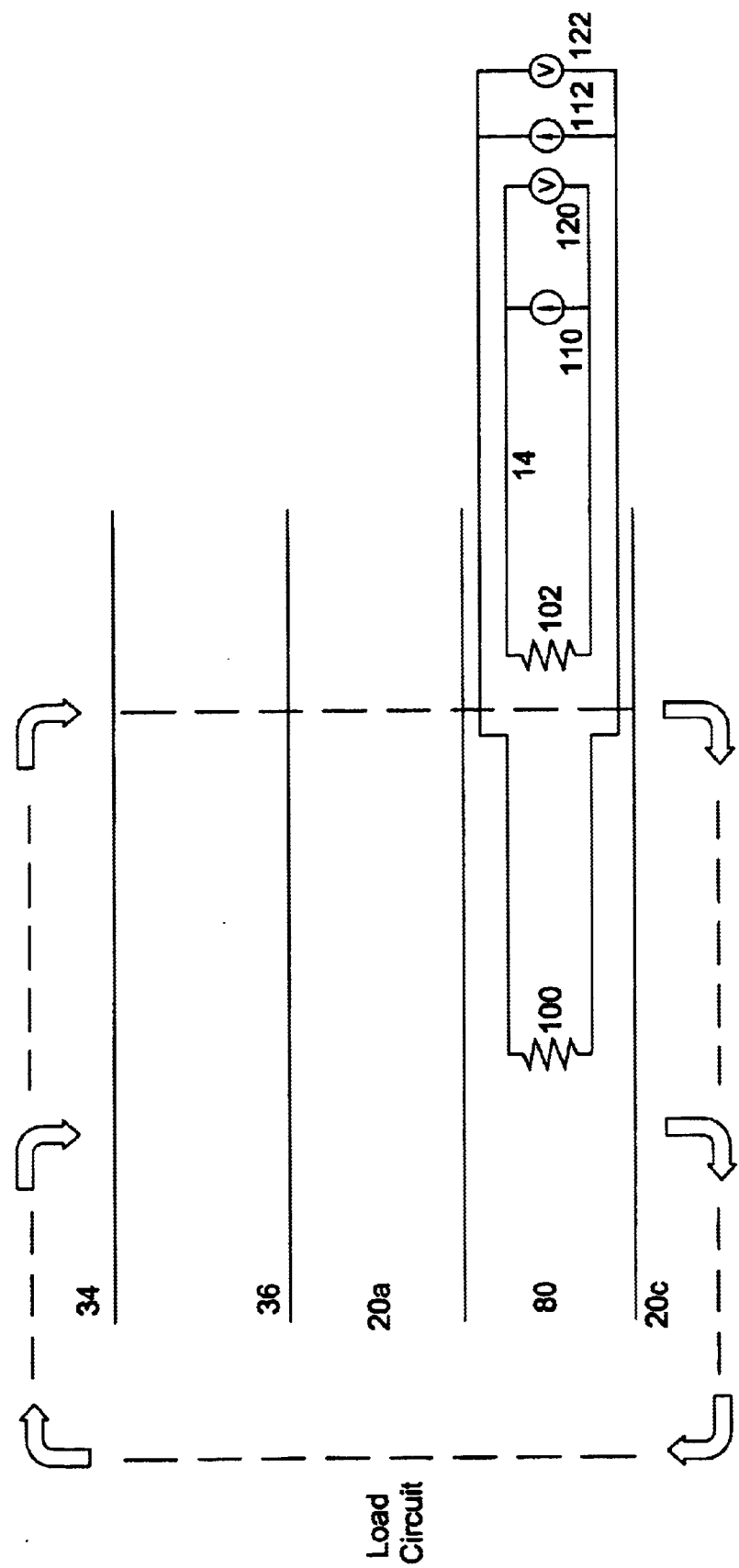
FIG. 5 is an illustration of the instrumentation for monitoring the temperature distribution plus voltage monitoring instrumentation.

In another embodiment, temperature distribution of a fuel cell is monitored in a manner similar to that described for current distribution. This is accomplished by placing thermistors in an array similar to the current-sensing resistors described above. FIG. 5 is a schematic illustration of a fuel cell incorporating the temperature distribution sensor plate 14, that includes voltage monitoring instrumentation.

It should be noted that the fuel cell load circuit and the temperature-sensing circuit are electrically isolated from one another. However, thermal energy produced in the load circuit is transferred through to the assembly, thus the load circuit and the temperature-sensing circuits are thermally connected. In other words, the temperature environment of the MEA in the load circuit is essentially the same temperature environment to which the thermistor, in the temperature-sensing circuit, is exposed.

To determine the temperature at any given point along the MEA 34, a known current is delivered to thermistors 100 and 102 by current sources 110 and 112 which is drawn from an external load. The voltage drop across thermistors 100 and 102 is measured by DC voltmeters 120 and 122. With knowledge of the temperature coefficients of the thermistors 100 and 102 and the current flowing therethrough, the analog voltage drops of the thermistors 100 and 102 is measured by the DC voltmeters 120 and 122 and converted to values representing the temperature at the location of thermistors 100 and 102. The array of thermistors across the entire cross-sectional area of the flow field plate of a fuel cell permits the temperature distribution of a complete fuel cell to be monitored.

In a preferred embodiment, current monitoring and temperature monitoring is combined into a single sensor plate assembly. This embodiment is the most advantageous for three reasons: (1) only a single sensor plate is added to the fuel cell to obtain both current and temperature measurements, (2) the same high-channel DC voltmeter instrumentation is used for monitoring both the current and temperature measurements, by incorporating appropriate switching into the instrumentation, and (3) fewer sense leads may be used because such leads serve more than one purpose.

Figure 6A:
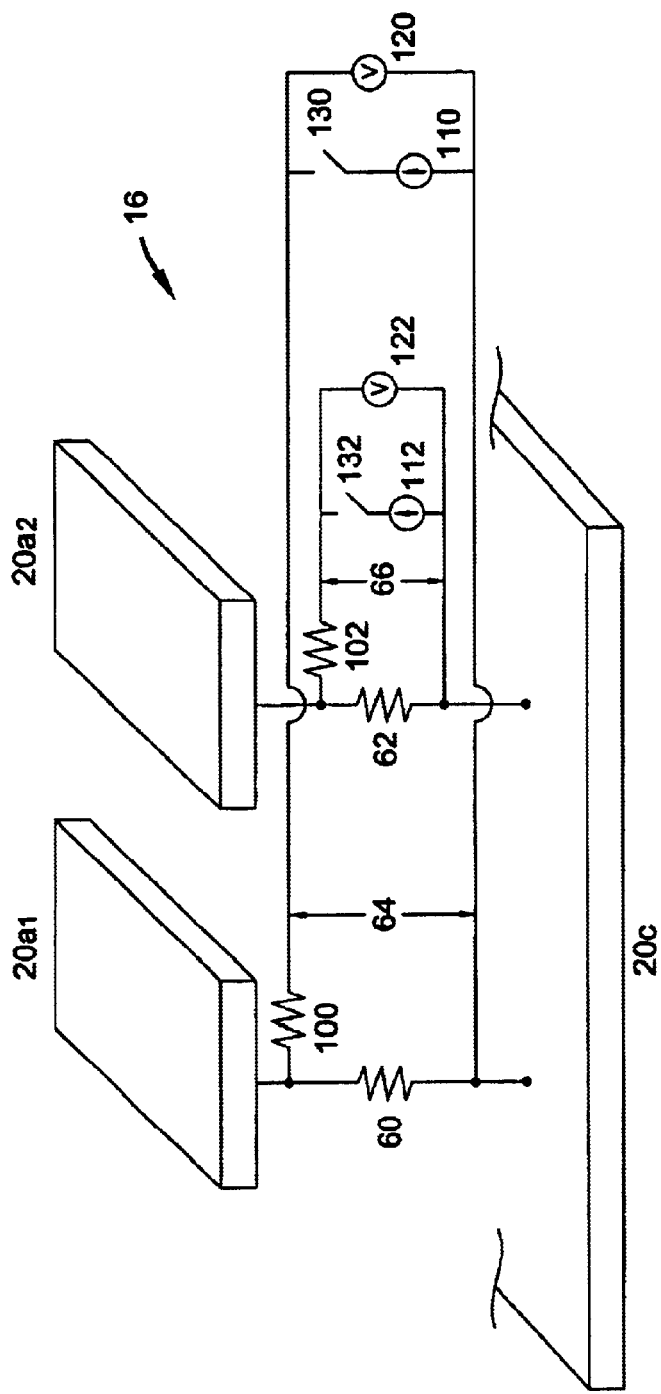
FIG. 6A is an illustration of the instrumentation for monitoring both the current and temperature distribution.

FIG. 6A is a schematic illustration of a fuel cell incorporating the current/temperature distribution sensor plate 16, including the monitoring instrumentation to support both measurements.

Segmented anode flow field plate elements 20$a_1$ and 20$a_2$ are connected to cathode flow field plate 20$a$ by current-sensing resistors 60 and 62. The resistors 60, 62 are connected to the voltage sense leads 64 and 66, via contact pads, and are extended back to the DC voltmeters 120 and 122, similar to the current distribution embodiment. In order to incorporate temperature measurement capability, thermistors 100 and 102 are inserted into one leg of the voltage sense lead pairs. Finally, a series combination of current sources 110 and 112 and switches 130 and 132 are added in parallel with DC voltmeters 120 and 122. The position of switches 130 and 132 determine whether current or temperature is being monitored.

When switches 130 and 132 are open, current sources 110 and 112 are electrically removed from the circuit. Because DC voltmeters 120 and 122 have a high impedance and the current-sensing resistors 60 and 62 have a low resistance, effectively all of the current leaving the segmented anode flow field plates 20$a_1$ and 20$a_2$ travels through the current-sensing resistors 60 and 62 to the cathode flow field plate 20$c$. Since current travels through the current-sensing resistor 60, 62 and not along the voltage sense leads 64 and 66, no voltage drop occurs across thermistors 100 and 102. In this way, DC voltmeters 120 and 122 monitor the voltage drop of current sensing resistors 60 and 62 without any effect from thermistors 100 and 102.

When switches 130 and 132 are closed, current sources 110 and 112 are electrically added to the circuit. Because current sources 110 and 112 are oriented to maintain current in a direction opposite to the load, no current leaving the anode flow field plate 20$a_1$ and 20$a_2$ travels through the thermistor branch of the circuit. Furthermore, current sources 110 and 112 maintain a known current flow through sense lead pairs 64 and 66, allowing a measurable voltage drop to occur across thermistors 100 and 102. In this configuration, DC voltmeters 120 and 122 monitor the sum of the voltage drops across thermistors 100 and 102 and current-sensing resistors 60 and 62.

It should be noted that current-sensing resistors 60 and 62 are selected to have low resistance values in order to inhibit or prevent lateral flow of current during current distribution measurement. By selecting thermistors 100 and 102 to have resistance values higher than that of the current-sensing resistors 60 and 62, the voltage drop across 60 and 62 becomes negligible. In this way, DC voltmeters 120 and 122 monitor the voltage drop of thermistors 100 and 102 without voltage contribution from current-sensing resistors 60 and 62.

Figure 6B:
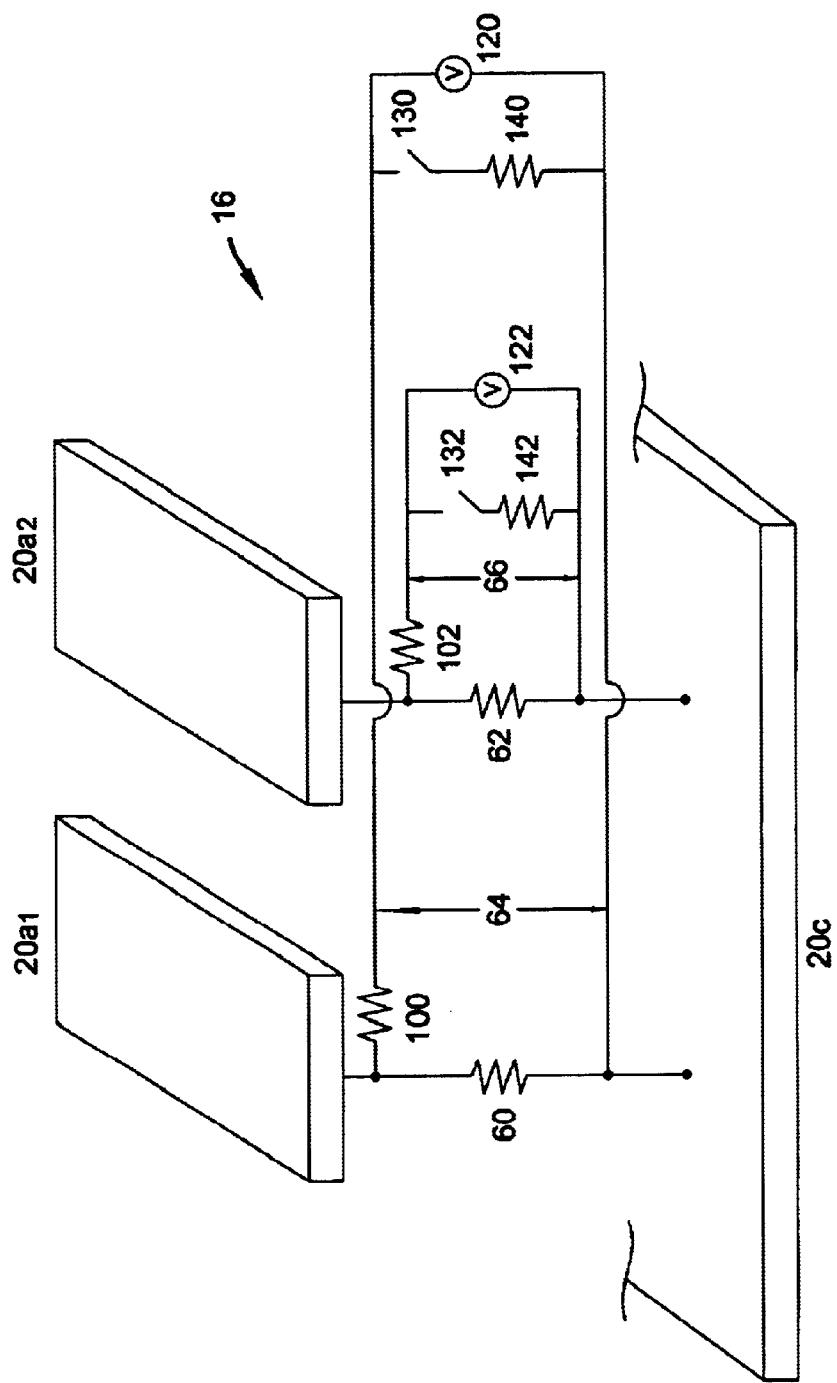
FIG. 6B is an illustration of the monitoring instrumentation for measuring current and temperature distribution using resistors instead of current sources.

In another embodiment, referring to FIG. 6B, current sources (110, 112 of FIG. 6) used for temperature measurement are replaced with a resistor 140, 142 which draws current from the load circuit of the fuel cell. In this embodiment, a small known current is drawn from the load circuit by a resistor 140, 142, instead of being added to the load circuit as described in the previous embodiment. This is accomplished by adding a reference resistor 140, 142 in series with the switch 130, 132, and by properly sizing both the reference resistor 140, 142 and thermistor 100, 102 so that their total resistance, relative to the shunt, is large enough to pull only a negligible current off of the load. Therefore, current drawn by the reference resistor 140, 142 is supplied by the load circuit created by the operation of the fuel cell. The values of the thermistor 100 and 102 and the reference resistor 140, 142 must also be proportionate, so that part of the voltage drop occurs across each of the reference resistors 140, 142 and the thermistors 100, 102.

By measuring the voltage with the switch open ($V_{open}$) and measuring the voltage drop with the switch closed ($V_{closed}$), the resistance of the thermistor can be calculated from the equation $R_{therm} = R((V_{open}/V_{closed})-1)$, where R equals the value of the replacement resistor.

Referring back to FIG. 4, the anode flow field plate 20$a$ is segmented into a plurality of electrically-isolated regions 86. The anode flow field plate 20$a$ is segmented by cutting separate channels using a cutting device, such as a laser jet cutter, leaving only a minor attachment at the corners thereof. Care is used to ensure that the flow field of the segmented plate is not disrupted. Segmenting the anode flow field plate 20$a$ electrically-isolates the segmented regions 20$a_1$, 20$a_2$ of the anode flow field plate 20$a$. After the anode flow field plate 20$a$ is segmented, it is electrically coupled to the circuit board by soldering or other suitable means. At this point, the minor attachments remaining at the corners of the segmented plate are cut using a cutting device, allowing the electrically isolated regions 86 of the anode flow field plate 20$a$ to be completely isolated from one another. Any disruptions in the flow field may be eliminated by locally filling the region with an epoxy or the like to preserve the integrity of the flow field.

The anode flow field plate 20$a$ has connection points 88 located within each electrically-isolated region 86 wherein the first connection lead of a current-sensing resistor 60, 62 associated with that electrically isolated region 86 can connect to the anode flow field plate 20$a$.

Figure 7:
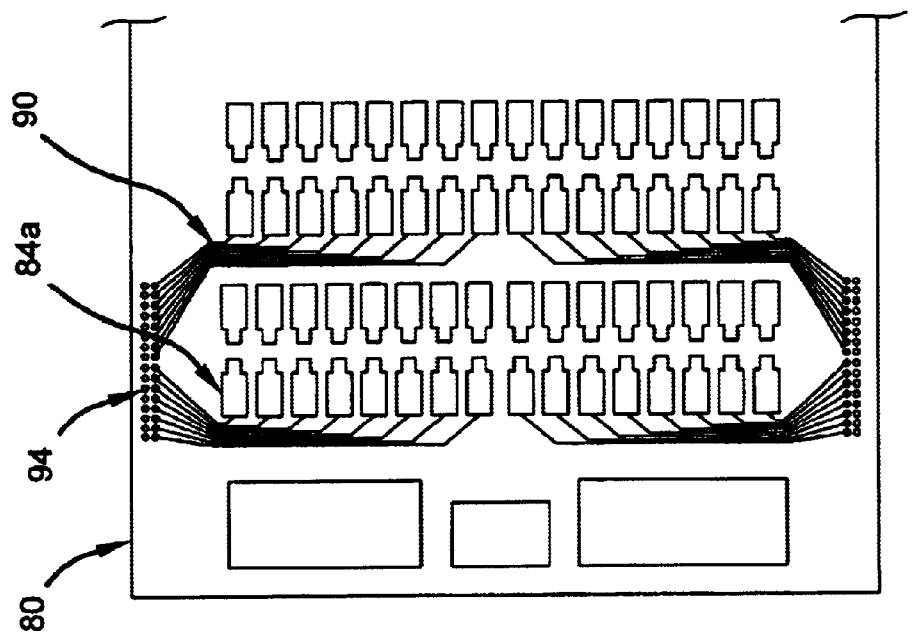
FIG. 7 is a partial view of a portion of the circuit board showing the electrical traces for coupling the resistors to a terminal block.

With reference to FIG. 7, the circuit board 80 is shown with electrical traces 90 connecting the contact pads (only 84$a$ is shown) and extending to an edge connector or terminal block 94.

Figure 8:
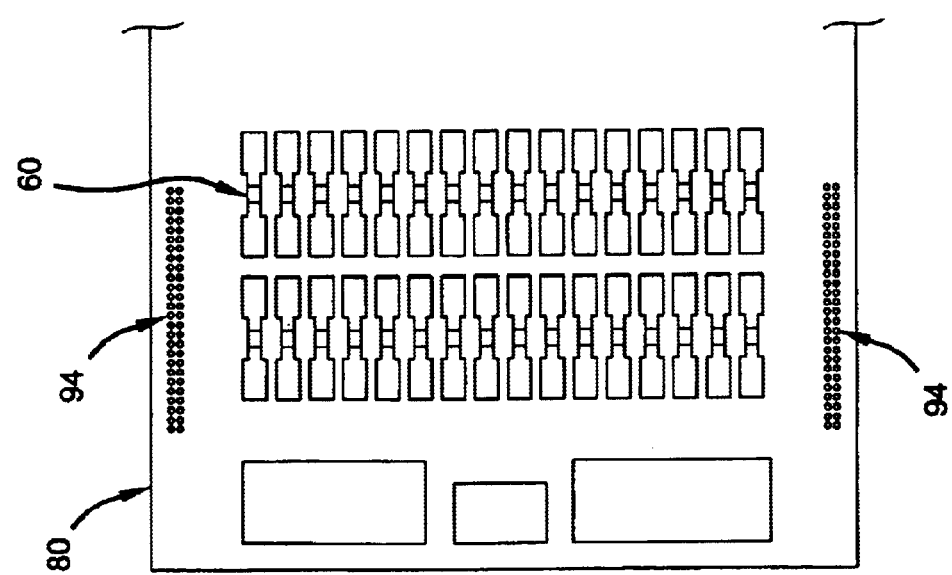
FIG. 8 is a top view of a portion of the resistor array located on the circuit board.

With reference now to FIG. 8, a portion of the circuit board 80 is shown wherein the current-sensing resistors 60, 62 are arranged in an array. A skilled practitioner will understand that the number and arrangement of the current-sensing resistor array may be modified in accordance with the size and the configuration of the flow field plate to be measured. In this regard, the resistors can be arranged in any manner that is appropriate to the design of the flow field and the segmented regions of the flow field plate.

Figure 9:
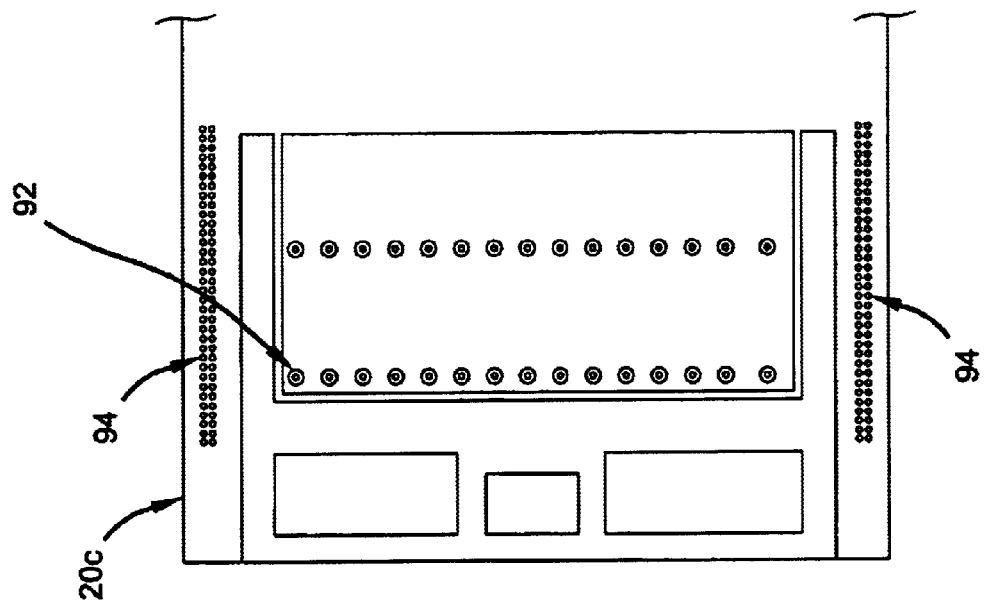
FIG. 9 is a top view of a portion of the connections points for the second connection lead of the resistor to the second flow field plate.

With reference now to FIG. 9, the cathode flow field plate 20$c$ is shown with the connection points 92 that correspond to the second connection lead of a current-sensing resistor 60, 62 associated with that electrically-isolated region 86.

This description of the invention is merely exemplary in nature and, thus, variations that do not depart from the gist of the invention are intended to be within the scope of the invention. Such variations are not to be regarded as a departures from the spirit and scope of the invention. In this regard, it should be noted that references to direction such as up, down, above, and below are merely for ease of illustrating the invention. Fuel cells stacks are arranged in any orientation, as are its elements, therefore, reference to direction is not meant to limit the invention.

What is claimed is:

1. A sensor assembly for measuring an operating parameter of a fuel cell comprising:
   a first flow field plate segmented into a plurality of electrically isolated regions;
   a second flow field plate; and
   a circuit board interposed between the first and second flow field plates and having a resistor array including a resistor associated with each of said plurality of electrically isolated regions for measuring the current flowing through the electrically isolated regions.

2. The sensor assembly of claim 1, wherein said resistor further comprises a first connection lead coupled between the resistor and the electrically isolated region of said first flow field plate.

3. The sensor assembly of claim 2, wherein said resistor further comprises a second connection lead coupled between the resistor and a common.

4. The sensor assembly of claim 2, wherein said resistor further comprises a second connection lead coupled between the resistor and the second flow field plate.

5. The sensor assembly of claim 1, further comprising a plurality of contact pads on the circuit board, each of said plurality of contact pads connected to a voltage sense lead of the resistor associated with the electrically isolated region for connecting to a measuring device.

6. The sensor assembly of claim 5, further comprising a thermistor in series with the voltage sense lead of the resistor.

7. The sensor assembly of claim 6, further comprising an electrical trace on the circuit board connected to the voltage sense lead of the thermistor for connecting to a measuring device.

8. The sensor assembly of claim 6, further comprising an electrical trace on the circuit board connected to a second voltage sense lead of the thermistor for connecting to a measuring device.

9. The sensor assembly of claim 6, further comprising a plurality of electrical traces on the circuit board, each of said plurality of electrical traces connected to one of the plurality of contact pads on the circuit board for connecting the resistor to a measuring device.

10. The sensor assembly of claim 9, wherein the electrical trace includes an edge connector.

11. The sensor assembly of claim 1, wherein the circuit board comprises an electrically non-conductive material.

12. A sensor assembly for measuring an operating parameter of a fuel cell comprising:
   a first flow field plate having a plurality of flow channels formed in a face for distributing reactant and having a plurality of regions;
   a circuit board associated with said flow field plate and having a thermistor array defining a plurality of regions of the fuel cell, including a thermistor associated with each of said plurality of regions for measuring temperature thereof.

13. The sensor assembly of claim 12, wherein said thermistor further comprises at least one of a first and second connection lead coupling the thermistor of the thermistor array to a measuring device.

14. The sensor assembly of claim 12, wherein the circuit board further comprises a plurality of contact pads connecting at least one of a first and second voltage sense lead of the thermistor to a measuring device.

15. The sensor assembly of claim 12, wherein said thermistor further comprises at least one of a first and second voltage sense lead connecting said thermistor to a measuring device.

16. The sensor assembly of claim 14, further comprising a plurality of electrical traces on the circuit board each of said plurality of traces connecting one of the plurality of contact pads on the circuit board to a measuring device.

17. The sensor assembly of claim 16, wherein the electrical trace includes an edge connector.

18. The sensor assembly of claim 12, wherein the circuit board comprises an electrically non-conductive material.

19. The sensor assembly of claim 12, wherein the first flow field plate is segmented into a plurality of electrically isolated regions.

20. The sensor assembly of claim 12, wherein the circuit board is interposed between said first flow field plate and a second flow field plate.

21. A sensor assembly for measuring an operating parameter of a fuel cell comprising:
   a first flow field plate having a plurality of regions;
   a circuit board associated with said flow field plate and having thermistor array defining a plurality of regions of the fuel cell, including a thermistor associated with each of said plurality of regions for measuring temperature thereof, and
   which further comprises a source of electrical current external of the fuel cell, said source of electrical current being delivered to said thermistor for measuring the voltage drop across the thermistor.

22. A sensor assembly for measuring an operating parameter of a fuel cell comprising:
   a first flow field plate having a plurality of regions;
   a circuit board associated with said flow field plate and having a thermistor array defining a plurality of regions of the fuel cell, including a thermistor associated with each of said plurality of regions for measuring temperature thereof, and
   further comprising a reference resistor for drawing current from a load circuit of the fuel cell, and delivering said current to each of said thermistor in said thermistor array for measuring the voltage drop across said thermistor.

23. A sensor assembly for measuring an operating parameter of a fuel cell comprising:
   a first flow field plate segmented into a plurality of electrically isolated regions;
   a second flow field plate;
   a circuit board interposed between the first and second low field plates and having a resistor array including a resistor associated with each of said plurality of electrically isolated regions for measuring the current flowing through the electrically isolated regions;
   each of said resistors having first and second connection leads, wherein the first connection lead connects the resistor to the first flow field plate and the second connection lead connects the resistor to the second flow field plate;
   each of said resistors having a voltage sense lead wherein a thermistor is connected thereto for measuring the temperature of the electrically isolated regions; and
   a source of current external of the fuel cell, delivered to said thermistor for measuring the voltage drop across the thermistor.

24. A sensor assembly for measuring an operating parameter of a fuel cell comprising:

a first flow field plate segmented into a plurality of electrically isolated regions;

a second flow field plate;

a circuit board between the first and second flow field plates and having a resistor array including a resistor associated with each of said plurality of electrically isolated regions for measuring the current flowing through the electrically isolated regions;

each of said resistors having first and second connection leads, wherein the first connection lead connects the resistor to the first flow field plate and the second connection lead connects the resistor to the second flow field plate;

each of said resistors having a voltage sense lead wherein a thermistor is connected thereto for measuring the temperature of the electrically isolated regions; and a reference resistor in series with each said thermistor, whereby the load resistor draws current from a load circuit for measuring the voltage drop across the thermistor.

* * * * *